US00RE48593E

(19) United States
(12) Reissued Patent
Hourmand et al.

(10) Patent Number: US RE48,593 E
(45) **Date of Reissued Patent: *Jun. 15, 2021**

(54) AUTO-INJECTOR

(71) Applicant: Sanofi-Aventis Deutschland GMBH, Frankfurt am Main (DE)

(72) Inventors: Yannick Hourmand, Haslingfield (GB); Simon Francis Brereton, Cambridge (GB); Matthew Ekman, Macclesfield (GB)

(73) Assignee: Sanofi-Aventis Deutschland GMBH, Frankfurt am Main (DE)

( * ) Notice: This patent is subject to a terminal disclaimer.

(21) Appl. No.: 16/749,698

(22) Filed: Jan. 28, 2020

Related U.S. Patent Documents

Reissue of:
(64) Patent No.: 9,272,098
Issued: Mar. 1, 2016
Appl. No.: 13/993,534
Filed: Dec. 21, 2011

U.S. Applications:
(63) Continuation of application No. 15/905,435, filed on Feb. 26, 2018, now Pat. No. Re. 47,903, which is an application for the reissue of Pat. No. 9,272,098.
(Continued)

(30) Foreign Application Priority Data

Dec. 21, 2010 (EP) ..... 10196070

(51) Int. Cl.
*A61M 5/20* (2006.01)
*A61M 5/32* (2006.01)
(Continued)

(52) U.S. Cl.
CPC ..... *A61M 5/2033* (2013.01); *A61M 5/20* (2013.01); *A61M 5/24* (2013.01); *A61M 5/326* (2013.01);
(Continued)

(58) Field of Classification Search
CPC ..... A61M 5/2033; A61M 5/24; A61M 5/326; A61M 5/3257; A61M 5/20; A61M 2205/581; A61M 2205/582; A61M 5/46
See application file for complete search history.

(56) References Cited

U.S. PATENT DOCUMENTS 6,004,297 A 12/1999 Steenfeldt-Jensen et al.
6,277,099 B1 8/2001 Strowe et al.
(Continued)

FOREIGN PATENT DOCUMENTS

DE 19819409 11/1999
DE 202007000578 3/2007
(Continued)

OTHER PUBLICATIONS

PCT International Preliminary Report on Patentability in International Appln. No. PCT/EP2011/073503, dated Jun. 25, 2013, 7 pages.
(Continued)

*Primary Examiner* — William C Doerrler
(74) *Attorney, Agent, or Firm* — Fish & Richardson P.C.

(57) ABSTRACT

[An auto-injector for administering a dose of a liquid medicament (M) comprises of a substantially cylindrical housing arranged to contain a pre-filled syringe with an injection needle, a plunger and a stopper for sealing a syringe barrel and a drive means releasably coupled to the plunger for advancing the syringe in the proximal direction (P) for needle insertion into an injection site and for displacing the dose of medicament (M) into the injection site. The drive means is arranged to be decoupled from the plunger for advancing a needle shroud to a safe position (PS) to surround the injection needle after the injection. According to the invention, the drive means bears against a thrust collar arranged to be releasably coupled to the plunger
(Continued)

through a ramped engagement of a first tongue and a first recess so as to rotate the thrust collar on translation in proximal direction (P). At least one longitudinal gap (G1, G2) is provided for guiding at a first and/or second protrusion of the thrust collar to prevent a rotation of the thrust collar. A circumferential gap (G3) is arranged to allow the thrust collar to rotate out of engagement to the plunger on removal of the auto-injector from the injection site.] *An auto-injector includes a housing, a thrust member comprising a radial projection configured to engage a ramped surface within the housing when the thrust member is in a first rotational position and to disengage from the ramped surface when the thrust member is moved to a second rotational position, a drive spring disposed within the housing, and a needle shroud configured to* (*i*) *inhibit rotation of the thrust member when the needle shroud is in an extended positon and the thrust member is in the first rotational position,* (*ii*) *allow the thrust member to rotate from the first rotational position to the second rotational position when the needle shroud is in a retracted positon, and* (*iii*) *permit the thrust member, after the thrust member has been rotated to the second rotational position, to be moved axially by the drive spring.*

25 Claims, 4 Drawing Sheets

Related U.S. Application Data

(60) Provisional application No. 61/432,250, filed on Jan. 13, 2011.

(51) Int. Cl.
*A61M 5/24* (2006.01)
*A61M 5/46* (2006.01)

(52) U.S. Cl.
CPC ..... *A61M 5/3257* (2013.01); *A61M 5/46* (2013.01); *A61M 2205/581* (2013.01); *A61M 2205/582* (2013.01)

(56) References Cited

U.S. PATENT DOCUMENTS 6,620,137 B2 9/2003 Kirchhofer et al.
7,195,616 B2 3/2007 Diller et al.
7,291,132 B2 11/2007 DeRuntz et al.
7,297,135 B2 11/2007 Jeffrey
7,341,575 B2 3/2008 Rice et al.
7,597,685 B2 10/2009 Olson
7,678,085 B2 3/2010 Graf
7,717,877 B2 5/2010 Lavi et al.
7,771,398 B2 8/2010 Knight et al.
7,976,494 B2 7/2011 Kohlbrenner et al.
8,038,649 B2 10/2011 Kronestedt
8,048,037 B2 11/2011 Kohlbrenner et al.
8,062,255 B2 11/2011 Brunnberg et al.
8,083,711 B2 12/2011 Enggaard
8,276,583 B2 10/2012 Farieta et al.
8,323,238 B2 12/2012 Cronenberg et al.
8,357,125 B2 1/2013 Grunhut et al.
8,361,025 B2 1/2013 Lawlis et al.
8,366,680 B2 2/2013 Raab
8,376,993 B2 2/2013 Cox et al.
8,376,997 B2 2/2013 Hogdahl et al.
8,403,883 B2 3/2013 Fayyaz et al.
8,409,141 B2 4/2013 Johansen et al.
8,409,148 B2 4/2013 Fiechter et al.
8,439,864 B2 5/2013 Galbraith et al.
8,491,538 B2 7/2013 Kohlbrenner et al.
8,568,359 B2 10/2013 Carrel et al.
8,617,109 B2 12/2013 Kronestedt et al.
8,617,124 B2 12/2013 Wieselblad et al.
8,632,507 B2 1/2014 Bartha
8,684,969 B2 5/2014 Moller et al.
8,708,973 B2 5/2014 Holmqvist
8,734,402 B2 5/2014 Sharp et al.
8,758,292 B2 6/2014 Tschirren et al.
8,808,250 B2 8/2014 Eckman et al.
8,808,251 B2 8/2014 Raab et al.
8,821,451 B2 9/2014 Daniel
8,834,431 B2 9/2014 Kohlbrenner et al.
8,840,591 B2 9/2014 Raab et al.
8,858,510 B2 10/2014 Karlsson
8,882,723 B2 11/2014 Smith et al.
8,911,411 B2 12/2014 Nielsen
8,939,934 B2 1/2015 Brereton et al.
8,945,063 B2 2/2015 Wotton et al.
8,956,331 B2 2/2015 Johansen et al.
8,961,473 B2 2/2015 Heald
8,968,256 B2 3/2015 Raab
8,968,258 B2 3/2015 Nzike et al.
8,992,484 B2 3/2015 Radmer et al.
8,992,487 B2 3/2015 Eich et al.
9,011,386 B2 4/2015 Kronestedt et al.
9,005,160 B2 5/2015 Karlsson et al.
9,011,387 B2 5/2015 Eckman et al.
9,022,991 B2 5/2015 Moeller
9,022,993 B2 5/2015 Dasbach et al.
9,022,994 B2 5/2015 Moser et al.
9,044,548 B2 6/2015 Miller et al.
9,044,553 B2 6/2015 James et al.
9,057,369 B2 6/2015 Kohlbrenner et al.
9,061,104 B2 6/2015 Daniel
9,067,024 B2 6/2015 Roberts et al.
9,089,652 B2 7/2015 Nzike et al.
9,108,002 B2 8/2015 Markussen
9,125,988 B2 9/2015 Karlsson
9,132,235 B2 9/2015 Holmqvist
9,199,038 B2 12/2015 Daniel
9,205,199 B2 12/2015 Kemp et al.
9,216,251 B2 12/2015 Daniel
9,220,841 B2 12/2015 Daniel
9,233,214 B2 1/2016 Kemp et al.
9,233,215 B2 1/2016 Hourmand et al.
9,242,044 B2 1/2016 Markussen
9,272,098 B2 3/2016 Hourmand et al.
9,283,326 B2 3/2016 Kemp et al.
9,283,327 B2 3/2016 Hourmand et al.
9,308,327 B2 4/2016 Marshall et al.
9,333,304 B2 5/2016 Brereton et al.
9,339,607 B2 5/2016 Langley et al.
9,352,088 B2 5/2016 Eckman et al.
9,358,345 B2 6/2016 Brereton et al.
9,358,351 B2 6/2016 Eckman et al.
9,393,368 B2 6/2016 Nzike et al.
9,408,897 B2 8/2016 Levinson et al.
9,408,977 B2 8/2016 Butler et al.
9,408,979 B2 8/2016 Veasey et al.
9,415,165 B2 8/2016 Cowe
9,421,336 B2 8/2016 Eckman et al.
9,427,525 B2 8/2016 Barrow-Williams et al.
9,446,196 B2 9/2016 Hourmand et al.
9,446,201 B2 9/2016 Holmqvist
9,457,149 B2 10/2016 Kemp et al.
9,457,152 B2 10/2016 Raab et al.
9,492,622 B2 11/2016 Brereton et al.
9,662,452 B2 5/2017 Daniel
9,713,677 B2 7/2017 Daniel
RE47,903 E * 3/2020 Hourmand ..... A61M 5/24
2002/0007154 A1 1/2002 Hansen et al.
2002/0095120 A1 7/2002 Larsen et al.
2005/0222539 A1 10/2005 Gonzales et al.
2005/0273055 A1 12/2005 Harrison et al.
2006/0153693 A1 7/2006 Fiechter et al.
2006/0287630 A1 12/2006 Hommann
2007/0027430 A1 2/2007 Hommann
2007/0112310 A1 5/2007 Lavi et al.
2007/0129686 A1* 6/2007 Daily et al. ..... 604/192

(56) References Cited

U.S. PATENT DOCUMENTS

| | | | | |
|---|---|---|---|---|
| 2010/0185178 | A1 | 7/2010 | Sharp et al. | |
| 2010/0280460 | A1* | 11/2010 | Markussen | 604/195 |
| 2010/0305512 | A1 | 12/2010 | Guillermo et al. | |
| 2011/0092915 | A1 | 4/2011 | Olson et al. | |
| 2011/0152781 | A1 | 6/2011 | Brunnberg et al. | |
| 2011/0313364 | A1 | 12/2011 | Rolfe et al. | |
| 2012/0010575 | A1 | 1/2012 | Jones et al. | |
| 2012/0041387 | A1 | 2/2012 | Bruggemann et al. | |
| 2012/0172817 | A1 | 7/2012 | Bruggemann et al. | |
| 2013/0035647 | A1 | 2/2013 | Veasey et al. | |
| 2013/0041328 | A1 | 2/2013 | Daniel | |
| 2013/0123710 | A1 | 5/2013 | Ekman et al. | |
| 2013/0131590 | A1 | 5/2013 | Olson et al. | |
| 2013/0261556 | A1 | 10/2013 | Jones et al. | |
| 2013/0274662 | A1 | 10/2013 | Hourmand et al. | |
| 2013/0274677 | A1 | 10/2013 | Eckman et al. | |
| 2013/0289525 | A1 | 10/2013 | Kemp et al. | |
| 2013/0310759 | A1 | 11/2013 | Hourmand et al. | |
| 2013/0345643 | A1 | 12/2013 | Hourmand et al. | |
| 2014/0288504 | A1 | 9/2014 | Karlsson et al. | |
| 2015/0100029 | A1 | 4/2015 | Cowe et al. | |
| 2015/0273157 | A1 | 10/2015 | Kohlbrenner et al. | |
| 2016/0089498 | A1 | 3/2016 | Daniel | |

FOREIGN PATENT DOCUMENTS

| | | |
|---|---|---|
| DE | 102005052502 | 5/2007 |
| EP | 0666084 | 8/1995 |
| EP | 0824923 | 2/1998 |
| EP | 0991441 | 12/2003 |
| EP | 2399634 | 12/2011 |
| EP | 2468334 | 6/2012 |
| EP | 2468335 | 6/2012 |
| WO | WO 1999/053979 | 10/1999 |
| WO | WO 2003/062672 | 7/2003 |
| WO | WO 2005/025636 | 3/2005 |
| WO | WO 2005/097238 | 10/2005 |
| WO | WO 2006/057604 | 6/2006 |
| WO | WO 2007/099044 | 9/2007 |
| WO | WO 2007/129324 | 11/2007 |
| WO | WO 2008/059385 | 5/2008 |
| WO | WO 2008/116688 | 10/2008 |
| WO | WO 2009/040607 | 4/2009 |
| WO | WO 2009/062508 | 5/2009 |
| WO | WO 2010/063707 | 6/2010 |
| WO | WO 2010/146358 | 12/2010 |
| WO | WO 2011/012903 | 2/2011 |
| WO | WO 2011/109205 | 9/2011 |
| WO | WO 2011/111006 | 9/2011 |
| WO | WO 2011/117592 | 9/2011 |
| WO | WO 2011/126439 | 10/2011 |
| WO | WO 2012/045350 | 4/2012 |
| WO | WO 2012/085024 | 6/2012 |

OTHER PUBLICATIONS

PCT International Search Report in International Appln. No. PCT/EP2011/073503, dated Mar. 9, 2012, 4 pages.

PCT International Preliminary Report on Patentability in International Application No. PCT/EP2011/073505, dated Jun. 25, 2013, 5 pages.

PCT International Search Report in International Application No. PCT/EP2011/073505, dated Jun. 15, 2012, 7 pages.

International Search Report for Int. App. No. PCT/EP2011/073505, completed Jun. 6, 2012.

* cited by examiner

AUTO-INJECTOR

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

The present application is a *continuation of U.S. reissue application Ser. No. 15/905,435, filed Feb. 26, 2018, and is also a reissue application of U.S. Pat. No. 9,272,098. U.S. reissue application Ser. No. 15/905,435 is a broadening reissue of U.S. application Ser. No. 13/993,534, filed Jun. 12, 2013, now U.S. Pat. No. 9,272,098, which is a* U.S. National Phase Application pursuant to 35 U.S.C. § 371 of International Application No. PCT/EP2011/073505 filed Dec. 21, 2011, which claims priority to European Patent Application No. 10196070.6 filed Dec. 21, 2010 and U.S. Provisional Patent Application No. 61/432,250 filed Jan. 13, 2011. The entire disclosure contents of these applications are herewith incorporated by reference into the present application.

TECHNICAL FIELD

The invention relates to an auto-injector for administering a dose of a liquid medicament.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

SUMMARY

It is an object of the present invention to provide an improved auto-injector.

The object is achieved by an auto-injector according to claim 1.

Preferred embodiments of the invention are given in the dependent claims.

In the context of this specification, the terms distal and proximal are defined from the point of view of a person receiving an injection. Consequently, a proximal direction refers to a direction pointing towards the body of a patient receiving the injection and a proximal end defines an end of an element that is directed towards the body of the patient. Respectively, the distal end of an element or the distal direction is directed away from the body of the patient receiving the injection and opposite to the proximal end or proximal direction.

An auto-injector for administering a dose of a liquid medicament comprises

- a substantially cylindrical housing arranged to contain a pre-filled syringe with an injection needle, a plunger and a stopper for sealing a syringe barrel and
- a drive means releasably coupled to the plunger for advancing the syringe in the proximal direction for needle insertion into an injection site and for displacing the dose of medicament into the injection site. The drive means is arranged to be decoupled from the plunger for advancing a needle shroud to a safe position to surround the injection needle after the injection.

According to the invention the drive means bears against a thrust collar arranged to be releasably coupled to the plunger through a ramped engagement so as to rotate the thrust collar on translation in the proximal direction, wherein guiding means are provided for guiding the thrust collar during at least a part of its axial translation when inserting the needle and displacing the medicament to prevent a rotation of the thrust collar, wherein the thrust collar is arranged to rotate out of engagement to the plunger on removal of the auto-injector from the injection site.

The ramped engagement between the thrust collar and the plunger may comprise a first tongue and a first recess engageable in a manner to rotate the thrust collar on translation in the proximal direction. At least one longitudinal gap may be provided as the guiding means for guiding a first or second protrusion of the thrust collar to prevent a rotation of the thrust collar. A circumferential gap may be arranged to allow the thrust collar to rotate out of engagement to the plunger on removal of the auto-injector from the injection site.

A crucial step in delivering medicaments with auto-injectors is the decoupling of the plunger from the drive means at the appropriate point in time. If the plunger is decoupled early, the dose of the medicament might not be completely expelled. Consequently, the medicament is partially wasted during the injection. However, such an early release might be necessary to ensure that the plunger is decoupled at the end of an injection stroke, so that in particular functions that ensure needle safety are reliably carried out. The injection mechanism of the auto-injector is designed in a manner that allows for a complete emptying of the syringe barrel containing the dose of the medicament before the plunger is decoupled from the drive means without compromising needle safety. According to the invention, the plunger is releasably coupled to a thrust collar. The coupling between the thrust collar and plunger is released upon rotation. The rotation between the thrust collar relative to the plunger may be caused by the first tongue engaging the first recess. No radial space is taken up for the release mechanism of the plunger and the thrust collar, so that the auto-injector may be designed in a particularly compact manner. Furthermore, the auto-injector comprises only a few parts and may thus be cost-efficiently produced.

At least one longitudinal gap may be provided that accommodates a first or second protrusion formed to the thrust collar. The first or second protrusion travels along the at least one gap when the thrust collar coupled to the plunger is driven proximally by the drive means, whereby a rotation of the thrust collar is prevented until the stopper, which is pushed proximally by the plunger to expel the dose of the medicament, reaches the proximal end of the syringe barrel and the first and/or second protrusion reaches the circumferential gap. The circumferential gap allows the thrust collar to rotate, whereby the thrust collar is decoupled from the plunger when the dose of medication has been completely injected and the auto-injector is removed from the injection site.

According to one possible embodiment of the invention, the thrust collar is releasably mounted to a coupling shroud rotationally fixed to the housing and firmly attached to the plunger. The coupling between the plunger and the thrust collar is released by disconnecting the thrust collar from the coupling shroud by rotating the thrust collar relative to coupling shroud.

According to another possible embodiment of the invention, the needle shroud is biased in the proximal direction towards an initial advanced position and slidable from the advanced position in a distal direction to a retracted position. In particular, the needle shroud may be slid to the retracted position by placing the auto-injector onto the skin of the patient receiving the injection and pressing the needle shroud against the skin of the patient. The needle shroud in the retracted position activates the delivery mechanism of the auto-injector delivering the medicament to the patient by releasing the drive means. The needle shroud is slidable from the retracted position in the proximal direction beyond the advanced position to the safe position, wherein the needle shroud surrounds the injection needle of the pre-filled syringe and protrudes beyond the needle tip in the proximal direction sufficient to prevent accidental needle stick injuries after the injection has been carried out.

Preferably, the needle shroud is arranged to prevent rotation of the thrust collar and thus release of the connection between the coupling shroud and the thrust collar until the dose of the medicament has been completely expelled and the auto-injector is withdrawn from the injection site. The auto-injector provides a reliable mechanism that covers the injection needle to avoid accidental needle stick injuries after the injection without wasting any medicament initially contained in the pre-filled syringe.

In one possible embodiment of the invention, the needle shroud incorporates a u-shaped indentation for receiving the second protrusion of the thrust collar in the retracted position. The second protrusion is retained in the u-shaped indentation to rotationally affix the thrust collar after full delivery of the medicament and until the needle shroud leaves the retracted position, which may in particular be achieved by removing the auto-injector from the injection site after the dose of the medicament has been injected. Thus, the needle shroud with the u-shaped indentation prevents the release of the connection between the thrust collar and the coupling shroud until the stopper has bottomed out and the injection is completed. The needle shroud is arranged to open the circumferential gap on translation into the advanced position for allowing the thrust collar to rotate out of engagement to the plunger. The auto-injector is suitable to be used for administering relative expensive medicaments as it is designed to completely empty the syringe barrel containing the dose of the medicament.

According to another possible embodiment of the invention, the needle shroud is releasably mounted to the housing by a clip preventing travel in the proximal direction beyond the advanced position. The thrust collar is disconnected from the coupling shroud at the end of the injection stroke delivering the medication. Upon the release, the thrust collar is driven proximally by the drive means to engage and deflect the clip to release the needle shroud. The needle shroud is then allowed to be moved in the proximal direction to the safe position, wherein the injection needle is covered to prevent accidental needle stick injuries.

According to another embodiment of the invention, a syringe retainer is arranged for mounting the syringe within the housing, wherein a retaining element is attached to the syringe retainer. The retaining element releasably couples the plunger to the syringe retainer. A force exerted upon the plunger by the drive means is thus directed via the retaining element to the syringe retainer, so that the syringe retainer carrying the pre-filled syringe may be moved in the proximal direction to insert the injection needle into the skin of the patient, whereby a displacement of the plunger relative to the syringe barrel containing the dose of the medicament is avoided. This prevents a premature expelling of the medicament before the injection needle penetrates the skin of the patient. Thus, unpleasant wet injections are avoided.

The retaining element may comprise at least one first catch that latches to a notch formed into the plunger to releasably couple the plunger to the syringe retainer. The first catch is released by a radial deflection and thus operates independently of the angular orientation of the coupling shroud and the thrust collar.

Preferably, the first catch is arranged to abut against an inner sleeve of the housing to prevent the decoupling of the plunger and the syringe retainer. An aperture is formed into the inner sleeve that allows for a radial outward deflection of the first catch to decouple the syringe retainer from the plunger. The aperture is located in a position that ensures that the decoupling takes place when the syringe retainer is in a proximal position and the injection needle protrudes from the proximal end of the auto-injection by a length that corresponds to a desired injection depth. The aperture is formed into the inner sleeve and is shielded by an outer casing of the housing. This prevents a user trying to re-use the auto-injector after an injection has been completed, by tampering with the first catch retained in the aperture. The auto-injector is designed as a single use device to minimize the risk of infections that are transmitted by needle stick injuries with used injection needles.

According to another possible embodiment of the invention, the coupling shroud comprises a flat first lateral wall that abuts against a corresponding flat second lateral wall of the inner sleeve to prevent a rotation of the coupling shroud relative to the housing. The interaction of the first and second lateral walls comprises a simple and effective means to ensure that the coupling shroud is rotationally affixed to the housing. This in turn ensures that the thrust collar may be reliably disconnected by a rotation about a relative small angle with respect to the coupling shroud.

According to yet another possible embodiment of the invention, a biasing means biases the needle shroud in the proximal direction. The biasing means and the drive means are fitted into each other to optimally use available space within the housing. This allows for a particular compact design of the auto-injector.

The biasing means is arranged as a compression spring having a diameter that differs from the diameter of the drive means in a manner that allows the drive means and the biasing means to expand independently from each other without interfering. The two nested compression springs provide a simple arrangement to efficiently use the space available within the housing of the auto-injectors and are inexpensive to produce.

According to yet another possible embodiment of the invention, the drive means is arranged as a single compression spring. The mechanism of the auto-injector is arranged in a manner that a plurality of functions is executed by the single drive means. The injection needle is inserted into the skin of the patient, the plunger is translated to expel the medicament and the needle shroud is moved proximally to provide needle safety after the injection is completed by the action of the spring means. Conventional auto-injectors usually comprise a plurality of spring means to accomplish these tasks. The auto-injector according to the invention comprises only few parts and is particularly inexpensive to mass-produce. Consequently, the auto-injector is particularly suited as a single-use device that may be disposed after an injection has been carried out.

In another possible embodiment of the invention, a rotating collar is arranged within the housing and axially fixed to the housing of the auto-injector. The rotating collar engages the needle shroud in a manner that forces the rotating collar to rotate within the housing when the needle shroud is axially displaced from the advanced position into the safe position. The rotating collar creates friction to slow down the proximal movement of the needle shroud that rests on the skin of the patient during the injection. The rotating collar acts as a dampening element that alleviates the pressure exerted upon the skin of the patient by the needle shroud. Thus, the risk of injuries is reduced and, in particular, bruises may be avoided. Furthermore, the modulus of resilience of the single drive means driving the needle shroud may be chosen to be sufficiently large without having to worry about potential injury risks. Thus, the modulus of resilience of the drive means is adapted to reliably provide an energy supply for executing a plurality of actions comprising, among others, the advancing and releasing of the needle shroud, the displacement of the stopper to expel the medicament and the decoupling of the plunger and the coupling shroud.

Preferably, the rotating collar comprises a pin that engages a track formed into the needle shroud. The track comprises a straight first section for guiding the pin between the retracted position and the advanced position and a second section oriented at an angle with respect to the first section for guiding the pin between the advanced position and the safe position. The pin travels along the track when the needle shroud is axially displaced. When the pin travels along the angled second section of the track, the rotating collar is forced to rotate around the needle shroud. This dampens the proximal movement of the needle shroud and thus reduces the pressure exerted upon the skin of the patient by generating friction.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
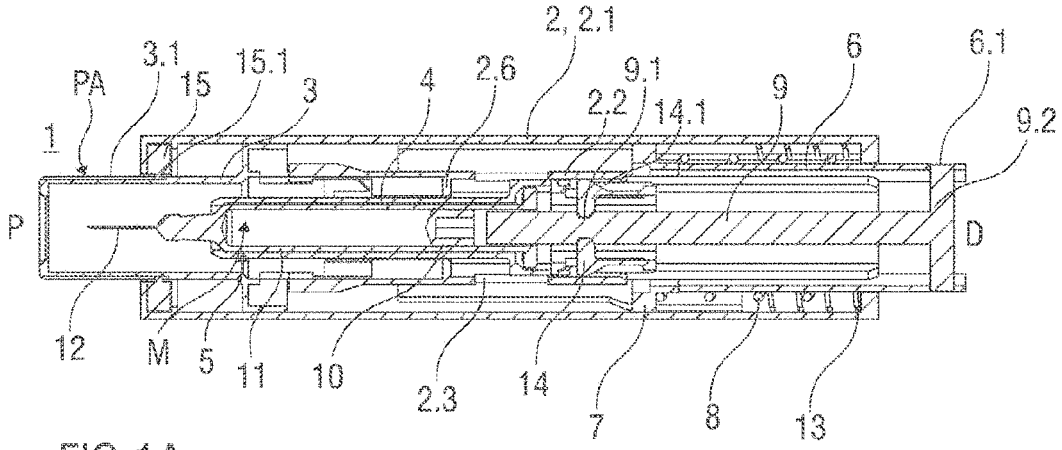
FIGS. 1A and 1B show two different sectional views of the auto-injector before an injection.
Figure 1B:
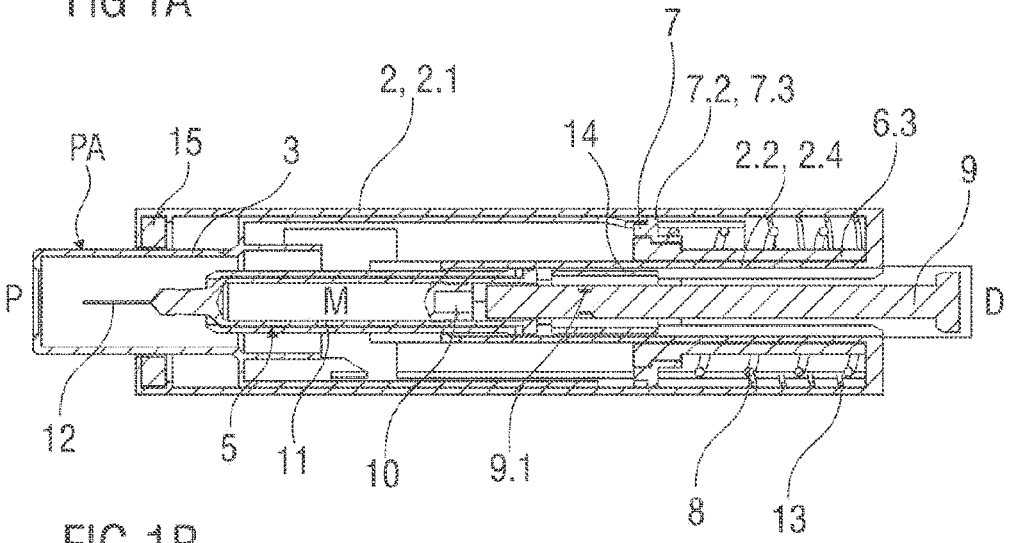

FIGS. 1A and 1B show two sectional views of an essentially cylindrical auto-injector 1, wherein the sectional planes shown are oriented perpendicularly with respect to each other. The auto-injector 1 comprises a housing 2, a proximal needle shroud 3, a syringe retainer 4 adapted to mount a pre-filled syringe 5 within the housing 2, a coupling shroud 6 slidably arranged within the housing 2 and a thrust collar 7 releasably connected to the coupling shroud 6 by a connection that is released by rotating the thrust collar 7 relative to the coupling shroud 6.

The releasable connection between the thrust collar 7 and the coupling shroud 6 is released by a rotation about a relative small angle around the axis of the substantially cylindrical auto-injector 1, like, for example, a quarter twist. The thrust collar 7 and the coupling shroud 6 may be connected by a bayonet kind of coupling or, alternatively, a thread connection with a corresponding lead that allows for a release by a relative small twist.

A drive means 8 is arranged between the distal end of the housing 2 and the thrust collar 7. The drive means 8 biases the thrust collar 7 in a proximal direction P towards the skin of a patient receiving an injection. The thrust collar 7 carries a threaded connection to the coupling shroud 6 with a steep pitch angle, and the coupling shroud 6 is restrained against rotation relative to the housing 2, so that the thrust collar 7 is additionally biased to rotate around the axis of the auto-injector 1.

According to one possible embodiment of the invention, the drive means 8 is arranged as a single, conventional compression spring.

The coupling shroud 6 is firmly attached to a plunger 9 arranged to push on a stopper 10 fluid-tightly sealing a distal end of a syringe barrel 11 containing a dose of a medicament M. A plunger collar 9.2 of the plunger 9 protrudes into a locking recess 6.1 formed into the distal end of the coupling shroud 6 to attach the plunger 9 to the coupling shroud 6.

An inner cavity of the syringe barrel 11 is in fluid communication with an injection needle 12, so that the dose of the medicament M may be expelled through the injection needle 12 by displacing the stopper 10 in the proximal direction P.

The needle shroud 3 is designed to be pushed against the skin of the patient during the injection. Edges of the needle shroud 3 may thus be smoothed to avoid injuries. The needle shroud 3 is slidably arranged with the housing 2 of the auto-injector 1, so that the needle shroud 3 may be pushed from an advanced position PA shown in FIGS. 1A and 1B in a distal direction D. A biasing means 13 bears against the needle shroud 3 and the distal end of the housing 2 to bias the needle shroud 3 towards the advanced position PA.

The biasing means 13 and the drive means 8 are fitted into each other to optimally use available space within the housing 2.

In a possible embodiment of the invention, the biasing means 13 is arranged as a compression spring having a diameter that differs from the diameter of the compression spring of the drive means 8 in a manner that allows the drive means 8 and the biasing means 13 to expand independently from each other without interfering.

A retaining element 14 is attached to a distal end of the syringe retainer 4 that releasably couples the plunger 9 to the syringe retainer 4, so that the syringe retainer 4 may jointly move with the plunger 9 in the proximal direction P to expose the injection needle 12. The retaining element 14 comprises at least one and preferably two or more first catches 14.1 arranged equi-spaced around retaining element 14, wherein each first catch 14.1 latches to a respective notch 9.1 formed into the plunger 9. The first catch 14.1 abuts against an inner sleeve 2.2 of the housing 2 in the radial outward direction, so that a deflection of the first catch 14.1 and hence a decoupling of the plunger 9 and the syringe retainer 4 is prevented.

The plunger 9 is coupled to the retaining element 14 and the syringe retainer 4 until the syringe retainer 4 mounting the pre-filled syringe 5 is moved proximally to expose the injection needle 12. A longitudinal aperture 2.3 is formed into the inner sleeve 2.2 of the housing 2 that allows for a radial outward deflection of the first catch 14.1 when the syringe retainer 4 is in a proximal position and the injection needle 12 is exposed. The plunger 9 is released from the retaining element 14 in the proximal position and may move proximally to displace the stopper 10, whereby the dose of medication M is expelled through the injection needle 12.

A ring-shaped rotating collar 15 is circumferentially arranged around a tubular proximal section of the needle shroud 3. A pin 15.1 is formed to an inner surface of the rotating collar 15 that engages a track 3.1 formed into an outer surface of the needle shroud 3. The track 3.1 comprises a straight first section 3.1.1 and a helical second section 3.1.2 that can best be seen in FIG. 5. The first section 3.1.1 of the track 3.1 extends essentially parallel to the axis of the auto-injector 1, whereas the second section 3.1.2 of the track 3.1 is angled with respect to the first section 3.1.1. As the needle shroud 3 is axially displaced with respect to the housing 2, the pin 15.1 travels along the track 3.1, so that the rotating collar 15 is forced to rotate around to the needle shroud 3. The friction generated by the rotation slows down the proximal movement of the needle shroud 3 and reduces pressure exerted upon the skin surface of the patient by the needle shroud 3.

Figure 2:
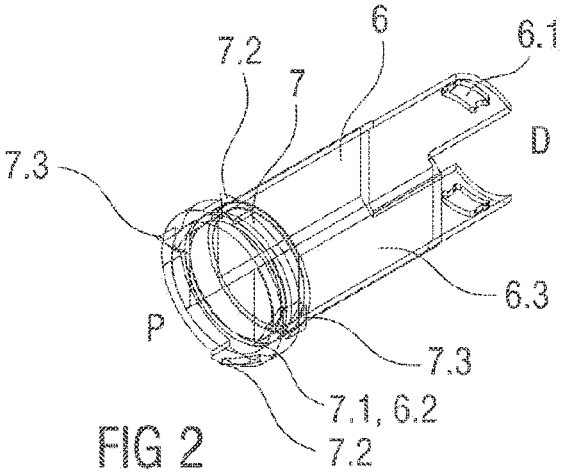
FIG. 2 shows in a perspective view a thrust collar connected to a coupling shroud by a thread connection.

FIG. 2 shows the coupling shroud 6 with the thrust collar 7 connected thereto in a perspective view. The connection between the thrust collar 7 and the coupling shroud 6 is releasable upon rotation. A helical first recess 6.2 is formed into an outer surface of the coupling shroud 6. A first tongue 7.1 that is correspondingly shaped to the first recess 6.2 is formed to an inner surface of the thrust collar 7. The first tongue 7.1 engages the first recess 6.2 to releaseably connect the coupling shroud 6 and the thrust collar 7 in a thread type connection.

The coupling shroud 6 is slidably arranged within the housing 2 and comprises a flat first lateral wall 6.3 that abuts a corresponding flat second lateral wall 2.4 of the inner sleeve 2.2 to prevent a rotation of the coupling shroud 6 relative to the housing 2.

The essentially ring-shaped thrust collar 7 comprises an outer surface with a plurality of first and second protrusions 7.2, 7.3 formed thereto. The first and second protrusions 7.2, 7.3 are circumferentially displaced from each other and protrude radially outwards. The first protrusions 7.2 have a quadrangular shape, whereas the second protrusion 7.3 comprises a triangular shape.

Figure 3:
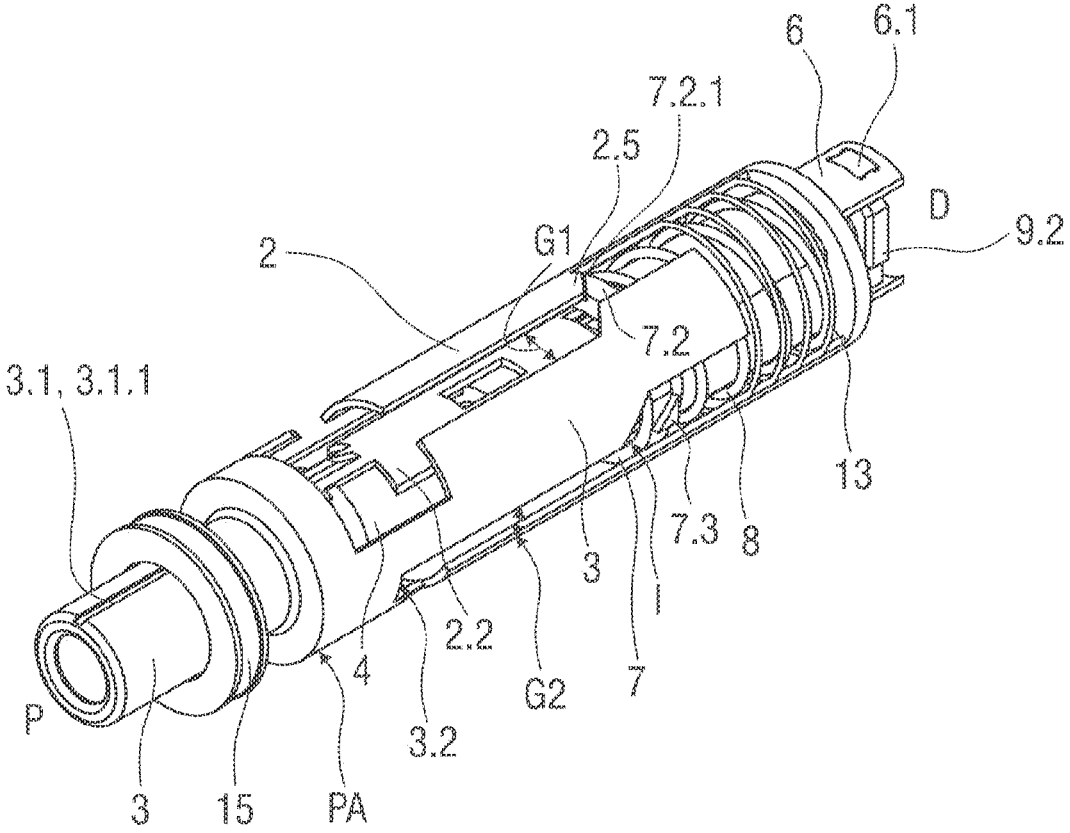
FIG. 3 shows an interior mechanism of the auto-injector in a perspective view before an injection.

FIG. 3 shows the auto-injector 1 in a perspective view before an injection is performed. For illustrative purposes, the outer shell 2.1 of the housing 2 is not shown. FIG. 3 illustrates an interior mechanism of the auto-injector 1 that is hidden from view by the outer case 2.2 during normal use. The needle shroud 3 is positioned in the advanced position PA.

The quadrangular first protrusion 7.2 comprises a first ramp 7.2.1 that abuts against a corresponding second ramp 2.5 formed to the housing 2. Furthermore, the first protrusion 7.2 abuts against the needle shroud 3 in a circumferential direction. Before the injection, the biased thrust collar 7 is retained in a first position I by the first protrusion 7.2 abutting against the needle shroud 3 and the second ramp 2.5 of the housing 2.

Figure 4:
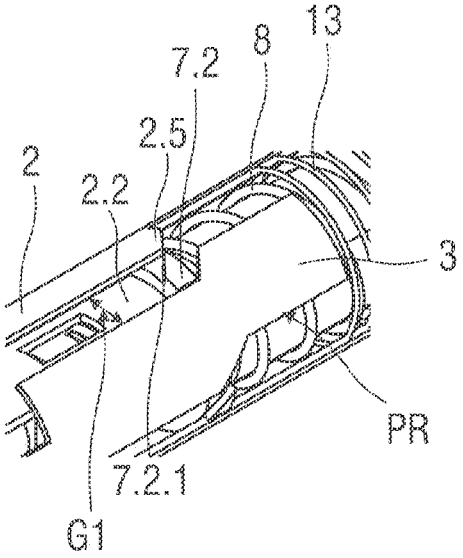
FIG. 4 shows details of the auto-injector that illustrate the release of a drive means in a perspective view.

The injection is initiated by pressing the needle shroud 3 against the skin of the patient receiving the injection, whereby the needle shield 3 is displaced from the advanced position PA in the distal direction D to a retracted position PR. As shown in detail in FIG. 4, the distal movement of the needle shroud 3 to the retracted position PR makes way for a circumferential displacement of first protrusion 7.2. The thrust collar 7 rotates around the axis of the auto-injector 1 by a small angle, insufficient to release thrust collar 7 from coupling shroud 6. The first protrusion 7.2 is guided by the first and second ramps 7.2.1, 2.5 into a longitudinal first gap G1 between the needle shroud 3 and the housing 2. The thrust collar 7 blocking the drive means 8 is now released. The fully compressed drive means 8 drives the thrust collar 7 and the coupling shroud 6 connected thereto in the proximal direction P, whereby the first protrusion 7.2 travels along the first gap G1 in the proximal direction P. At the same time the second protrusion 7.3 travels proximally along a longitudinal second gap G2 that is arranged between the housing 2 and the needle shroud 3 in a similar manner as the first gap G1. As the first Gap G1 is arranged to limit a circumferential displacement of the first protrusion 7.2, a further rotation of the thrust collar 7 is prevented until an injection stroke delivering the dose medication M is completed.

The thrust collar 7 is connected to the coupling shroud 6 that is attached to the plunger 9. The plunger 9 in turn is coupled to syringe retainer 4 via the retaining element 14. Thus, the coupling shroud 6 driven by the drive means 8 first translates the syringe retainer 4 holding the pre-filled syringe 5 in the proximal direction P until the syringe retainer 4 bears against a bearing surface 2.6 formed to the housing 2 as best seen in FIG. 1A. The bearing surface 2.6 defines an injection depth of the injection needle. The injection needle 12 now protrudes from the needle shroud 3 in the proximal direction P and penetrates the skin surface of the patient at the desired injection depth.

The deflectable first catches 14.1 that couple the plunger 9 to the syringe retainer 4 are now located adjacent to the longitudinal apertures 2.3 formed into the inner sleeve 2.2 of the housing 2. The first catches 14.1 deflect in the radial outward direction due to their ramped engagement with the notches 9.1 and disengage from the notches 9.1 to decouple the plunger 9 from the syringe retainer 4.

The drive means 8 further relaxes and drives the coupling shroud 6, the thrust collar 7 and the plunger 9 in the proximal direction P. The plunger 9 pushes the stopper 10 proximally to expel the dose of medication M contained in the syringe barrel 11 through the injection needle 12.

When the stopper 10 reaches a proximal end of the syringe barrel 11, the injection stroke is completed and the dose of medication M is completely expelled. At the same time, the thrust collar 7 reaches a proximal second position II shown in FIG. 5.

Figure 5:
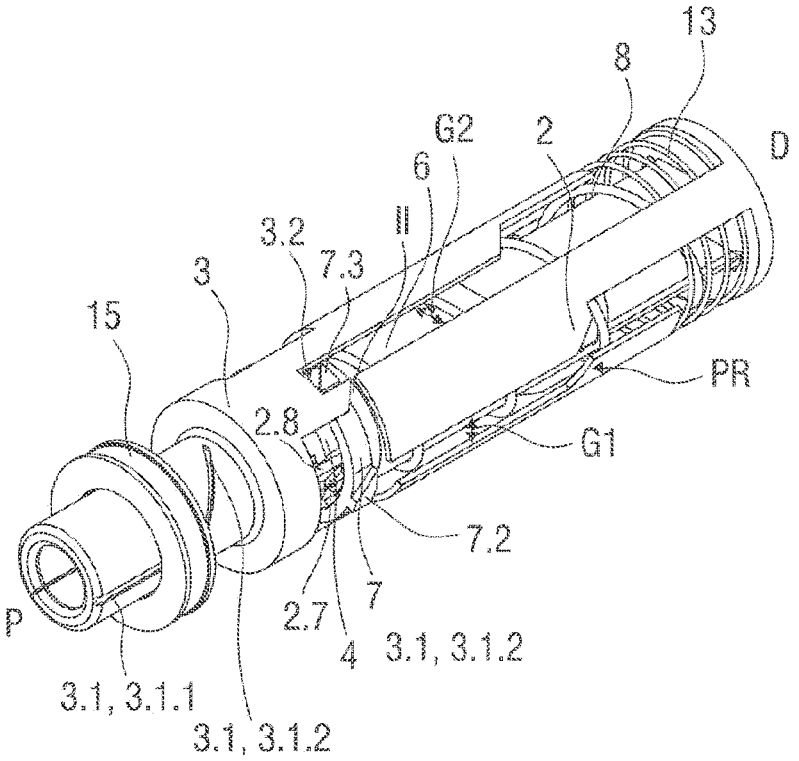
FIG. 5 shows the interior mechanism of the auto-injector in a perspective view after an injection stroke.

FIG. 5 shows the auto-injector 1 in a perspective view after the injection stroke is completed. Similar to FIGS. 3 and 4, the outer shell 2.1 is not shown to illustrate the interior mechanism of auto-injector 1.

The needle shroud 3 is still pressed against the injection site to retain the needle shroud 3 in the retracted position PR. At the same time, the thrust collar 7 is located in the second position II. The triangular second protrusion 7.3 of the thrust collar 7 is retained in a u-shaped indentation 3.2 formed to the needle shroud 3. The u-shaped indentation 3.2 constitutes a proximal end of the second gap G2 and comprises a circumferential width that corresponds to the second protrusion 7.3. The u-shaped indentation 3.2 abuts against the second protrusion 7.3 in the circumferential direction, so that a rotation of the thrust collar 7 and thus a decoupling of the thrust collar 7 and the coupling shroud 6 are prevented until the needle shield 3 leaves the retracted position PR.

The auto-injector 1 is removed from the injection site. The biasing means 13 relaxes to return the needle shroud 3 to the advanced position PA. As a consequence, the needle shroud 3 moves proximally with respect to the housing 2 and the thrust collar 7 connected to the coupling shroud 6.

Figure 6:
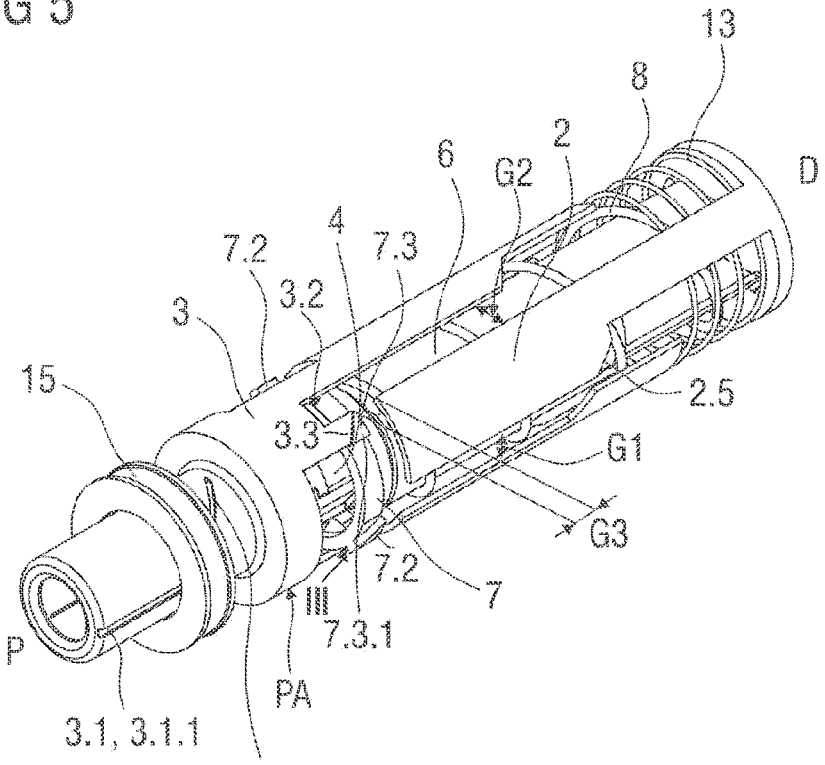
FIG. 6 shows the interior mechanism of the auto-injector in a perspective view, wherein the decoupling of the thrust collar and the coupling shroud is illustrated.

FIG. 6 shows the interior mechanism of the auto-injector 1 in a perspective view after the auto-injector 1 has been removed from the injection site. The proximal movement of the needle shroud 3 opens a circumferential gap G3 between the housing 2 and the needle shroud 3. The triangular second protrusion 7.3 travels through the circumferential gap G3 in the circumferential direction, whereby the thrust collar 7 slightly rotates around the axis of the auto-injector 1 due to the ramped engagement of the first tongue 7.1 with the first recess 6.2. The drive means 8 bears against the thrust collar 7 and pushes a third ramp 7.3.1 on the second protrusion 7.3 against a corresponding fourth ramp 3.3 on the needle shroud 3 when the thrust collar 7 is located in an intermediate third position III. The thrust collar 7 tries to rotate due to its threaded connection with the coupling shroud 6.1 relative to the housing 2 and relative to the coupling shroud 6. If a bayonet connection was used instead of the thread the third and fourth ramp 7.3.1, 3.3 would cause the thrust collar 7 to further rotate. This final rotation of the thrust collar 7 suffices to decouple the coupling shroud 6 and the thrust collar 7. The decoupled thrust collar 7 is then driven further in the proximal direction P by the drive means 8 until an inner surface of the thrust collar 7 engages a fifth ramp 2.7 of a clip 2.8 connecting the housing 2 with the needle shroud 3 that is shown in more detail in FIG. 7.

Figure 7:
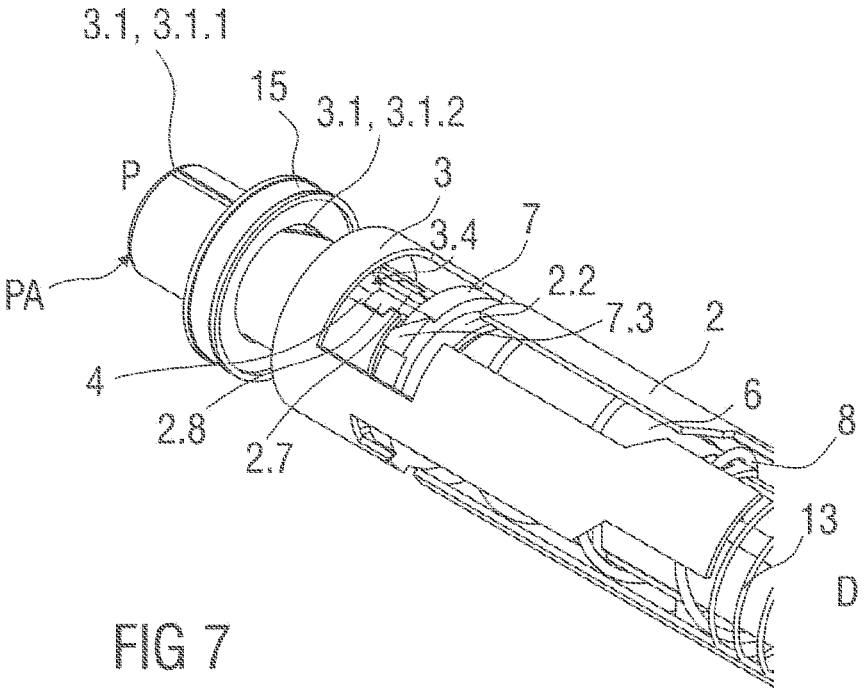
FIG. 7 shows details of the auto-injector that illustrate the release of a needle shroud.

FIG. 7 shows the release of the substantially t-shaped clip 2.8 that mounts the needle shroud 3 to the housing 2. The t-shaped clip 2.8 is retained in a second recess 3.4 formed in the needle shroud 3. The second recess 3.4 comprises axial dimensions that allow for a sliding movement of the needle shroud 3 relative to the housing 2 between the advanced position PA and the retracted position PR while the clip 2.8 is retained in the second recess 3.4.

The clip 2.8 is deflectable in the radial inward direction to release the needle shroud 3. As shown in FIG. 7, the thrust collar 7 slides over the fifth ramp 2.7 to bend the clip 2.8 radially inwards after the thrust collar 7 and coupling shroud 6 have been decoupled. The t-shaped clip 2.8 is deflected inwards and disengages from the second recess 3.4, so that the needle shroud 3 may be proximally advanced towards a safe position PS. The drive means 8 further relaxes and pushes the decoupled thrust collar 7 further in the proximal direction P. The thrust collar 7 bears against the needle shroud 3 to advance the needle shroud 3 towards the safe position PS shown in more detail in FIG. 8.

When the needle shield 3 moves proximally from the advanced position PA to the safe position PS, the pin 15.1 of the rotating collar 15 travels along the second section 3.1.2 of the track 3.1 formed into the needle shroud 3. As the second section 3.1.2 is oriented at an angle with respect to the axis of the auto-injector, the translatory movement of the needle shroud 3 causes the rotating collar 15 to rotate around the axis, whereby friction is generated. The generated friction slows down and damps the proximal movement of the needle shroud 3.

Figure 8:
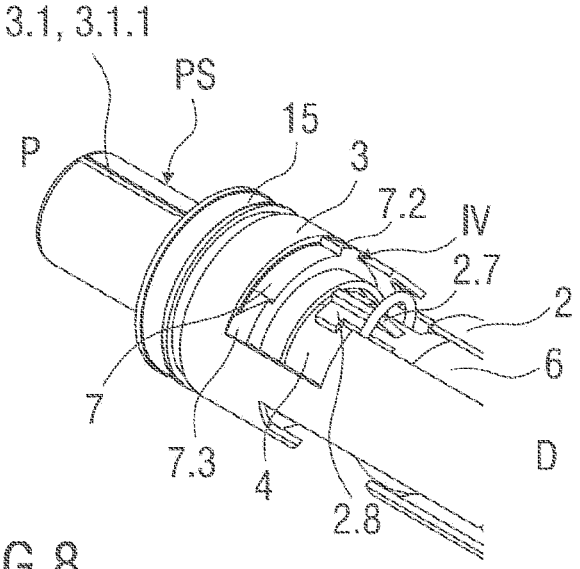
FIG. 8 shows details of the auto-injector that illustrate the locking of the needle shroud in a safe position.

FIG. 8 shows a perspective view of the interior mechanism of the auto-injector 1, wherein the needle shroud 3 is locked in the safe position PS. In the safe position PS, the needle shroud 3 protrudes proximally from the housing 2 of the auto-injector 1 and permanently surrounds and protrudes proximally beyond the tip of the injection needle 12 after an injection to prevent accidental needle stick injuries.

As the thrust collar 7 and the needle shroud 3 have travelled proximally beyond the clip 2.8, the clip 2.8 deflects outwards to return to its prior position. The needle shroud 3 abuts against the t-shaped clip 2.8 in the distal direction D, so that a distal movement of the needle shroud 3 in the safe position PS relative to the housing 2 is prevented. Thus, the needle shroud 3 is permanently locked in the safe position PS and a re-exposure of the injection needle 12 is prevented. The thrust collar 7 travelled over the fifth ramp 2.7 and is located in a maximum proximal fourth position IV, wherein the thrust collar 7 abuts the needle shroud 3.

The invention claimed is:

[1. Auto-injector for administering a dose of a liquid medicament (M), comprising:

a substantially cylindrical housing arranged to contain a pre-filled syringe with an injection needle, a plunger and a stopper for sealing a syringe barrel and a driver releasably coupled to the plunger for advancing the syringe in the proximal direction (P) for needle insertion into an injection site and for displacing the dose of medicament (M) into the injection site, wherein the driver is arranged to be decoupled from the plunger for advancing a needle shroud to a safe position (PS) to surround the injection needle after the injection, wherein the driver bears against a thrust collar arranged to be releasably coupled to the plunger through a ramped engagement so as to rotate the thrust collar on translation in proximal direction (P), wherein guiding mechanism are provided for guiding the thrust collar during at least a part of its axial translation when inserting the needle and displacing the medicament (M) to prevent a rotation of the thrust collar, wherein the thrust collar is arranged to rotate out of engagement to the plunger on removal of the auto-injector from the injection site.]

[2. Auto-injector according to claim 1, wherein the ramped engagement between the thrust collar and the plunger comprises a first tongue and a first recess, wherein the guiding mechanism comprises at least one longitudinal gap (GI, G2) for guiding a first or second protrusion of the thrust collar, wherein a circumferential gap (G3) is arranged to allow the thrust collar to rotate out of engagement to the plunger on removal of the auto-injector from the injection site.]

[3. Auto-injector according to claim 1, wherein the thrust collar is releasably mounted to a coupling shroud rotationally fixed to the housing and firmly attached to the plunger, wherein the connection between the thrust collar and the coupling shroud is releasable by a relative rotation between the thrust collar and the coupling shroud.]

[4. Auto-injector according to claim 1, wherein the needle shroud is biased in a proximal direction (P) towards an advanced position (PA) and slidable from the advanced position (PA) in a distal direction (D) to a retracted position (PR) and from the retracted position (PR) in the proximal direction (P) beyond the advanced position (PA) to the safe position (PS), wherein sliding the needle shroud from the advanced position (PA) to the retracted position (PR) releases the driver.]

[5. Auto-injector according to claim 4, wherein at the needle shroud in the refracted position (PR) is arranged to prevent rotation of the thrust collar, thus preventing the release of the connection between the thrust collar and the coupling shroud.]

[6. Auto-injector according to claim 5, wherein the needle shroud comprises au-shaped indentation for receiving the second protrusion of the thrust collar to prevent the release of the connection between the thrust collar and the coupling shroud in the retracted position (PR), wherein the needle shroud is arranged to open the circumferential gap (G3) on translation into the advanced position (PA) for allowing the thrust collar to rotate out of engagement to the plunger.]

[7. Auto-injector according to claim 1, wherein at the needle shroud is releasably mounted to the housing by a clip preventing travel in proximal direction (P) beyond the advanced position (PA), wherein the thrust collar is arranged to radially deflect the clip for releasing the needle shroud allowing it to be moved in the proximal direction (P) to the safe position (PS).]

[8. Auto-injector according to claim 1, wherein a syringe retainer is arranged for mounting the syringe within the housing, wherein a retaining element is attached to the syringe retainer, wherein the release element releasably couples the plunger to the syringe retainer.]

[9. Auto-injector according to claim 8, wherein the retaining element comprises at least one first catch that latches to a notch formed into the plunger to releasably couple the plunger to the syringe retainer. ]

[10. Auto-injector according to claim 8, wherein the first catch is arranged to abut against an inner sleeve of the housing to prevent decoupling of the plunger and the syringe retainer, wherein an aperture is formed into the inner sleeve allowing for a radial outward deflection of the first catch to decouple the syringe retainer from the plunger when the syringe retainer is in a proximal position.]

[11. Auto-injector according to claim 10, wherein the coupling shroud comprises a flat first lateral wall that abuts against a corresponding flat second lateral wall of the inner sleeve to prevent a rotation of the coupling shroud relative to the housing.]

[12. Auto-injector according to claim 1, wherein a biasing mechanism biases the needle shroud in the proximal direction (P), wherein the biasing mechanism and the driver are fit into each other to optimally use available space within the housing.]

[13. Auto-injector according to claim 1, wherein the driver is arranged as a single compression spring.]

[14. Auto-injector according to claim 13, wherein the single compression spring is strained only translationally.]

[15. Auto-injector according to claim 1, wherein a rotating collar axially fixed to the housing engages the needle shroud in a manner that forces the rotating collar to rotate within the housing when the needle shroud is axially displaced from the advanced position (PA) into the safe position (PS).]

[16. Auto-injector according to claim 1, wherein the rotating collar comprises a pin that engages a track formed into the needle shroud, wherein the track comprises a straight first section for guiding the pin between the retracted position (PR) and the advanced position (PA) and a helical second section for guiding the pin between the advanced position (PA) and the safe position (PS).]

*17. An auto-injector for administering a dose of a liquid medicament, the auto-injector comprising:*

*a housing configured to contain a syringe barrel of a syringe;*

*a thrust member comprising a radial projection, the radial projection configured to engage a ramped surface within the housing when the thrust member is in a first rotational position and to disengage from the ramped surface when the thrust member is moved to a second rotational position;*

*a drive spring disposed within the housing and configured to apply an axial force to the thrust member such that when the thrust member is in the first rotational posi-*

*tion, the engagement between the radial projection and the ramped surface biases the thrust member from the first rotational position toward the second rotational position; and*

*a needle shroud configured to move from an extended position to a retracted position, the needle shroud configured to (i) inhibit rotation of the thrust member relative to the needle shroud when the needle shroud is in the extended positon and the thrust member is in the first rotational position, (ii) allow the thrust member to rotate from the first rotational position to the second rotational position when the needle shroud is in the retracted positon and (iii) permit the thrust member, after the thrust member has been rotated to the second rotational position, to be moved axially by the drive spring.*

*18. The auto-injector of claim 17, wherein the ramped surface is a surface of the housing.*

*19. The auto-injector of claim 18, wherein the radial projection of the thrust member has a ramp that engages the ramped surface within the housing when the thrust member is in the first rotational position.*

*20. The auto-injector of claim 17, wherein the thrust member further comprises a second radial projection.*

*21. The auto-injector of claim 20, wherein the radial projection and the second radial projection are circumferentially spaced apart from one another about the thrust member.*

*22. The auto-injector of claim 20, wherein the needle shroud has a longitudinal surface configured to engage the second radial projection to inhibit rotation of the thrust member relative to the needle shroud.*

*23. The auto-injector of claim 22, wherein the needle shroud defines a circumferential opening configured to allow the second radial projection to rotate relative to the needle shroud.*

*24. The auto-injector of claim 20, wherein the needle shroud defines a longitudinal opening arranged to allow the second radial projection to move axially within the longitudinal opening when the thrust member, after having been rotated to the second rotational position, is moved axially by the drive spring.*

*25. The auto-injector of claim 17, wherein the thrust member comprises a plunger configured to contact a stopper of the syringe and advance the stopper within a chamber of the syringe to administer the dose of the liquid medicament when the thrust member is moved axially by the drive spring and the syringe is disposed in the housing.*

*26. The auto-injector of claim 17, wherein the thrust member is coupled to the syringe when the syringe is disposed in the housing, and the thrust member is configured to advance the syringe axially within the housing when the thrust member is moved axially by the drive spring.*

*27. The auto-injector of claim 17, wherein the needle shroud has a surface configured to engage the radial projection to inhibit rotation of the thrust member relative to the needle shroud when the needle shroud is in the extended positon and the thrust member is in the first rotational position.*

*28. The auto-injector of claim 27, wherein the surface of the needle shroud that is configured to engage the radial projection of the thrust member is a longitudinal surface that is configured to circumferentially engage the radial projection.*

*29. The auto-injector of claim 17, wherein the needle shroud defines an opening arranged to receive the radial projection when the needle shroud is in the retracted positon to allow the thrust member to rotate from the first rotational position to the second rotational position, and the opening is arranged to permit the radial projection to move axially within the opening when the thrust member has been rotated to the second rotational position and is moved axially by the drive spring.*

*30. The auto-injector of claim 29, wherein the opening of the needle shroud includes a first portion and a second portion, at least part of the second portion being circumferentially offset from the first portion.*

*31. The auto-injector of claim 30, wherein the first portion of the opening is defined at least in part by a surface of the needle shroud that is configured to engage the radial projection of the thrust member such that the radial projection resides within the first portion of the opening when the thrust member is in the first rotational position.*

*32. The auto-injector of claim 31, wherein the opening of the needle shroud is arranged to permit the radial projection of the thrust member to move axially within the second portion of the opening when the thrust member has been rotated to the second rotational position and is moved axially by the drive spring.*

*33. The auto-injector of claim 29, wherein the opening of the needle shroud is at least partially defined by an axially extending arm of the needle shroud.*

*34. The auto-injector of claim 33, wherein the needle shroud further comprises a cylindrical end body from which the axially extending arm extends.*

*35. The auto-injector of claim 34, wherein the needle shroud further comprises a second axially extending arm that extends axially from the cylindrical end body.*

*36. The auto-injector of claim 17, wherein the needle shroud is configured to move from the retracted position to a safe position in which the needle shroud extends forward of the housing, and a portion of the housing is configured to engage the needle shroud to lock the needle shroud in the safe position.*

*37. The auto-injector of claim 17, wherein the drive spring directly contacts the thrust member.*

*38. The auto-injector of claim 17, further comprising a needle shroud spring that biases the needle shroud toward the extended position.*

*39. The auto-injector of claim 17, further comprising the syringe disposed in the housing.*

*40. The auto-injector of claim 39, wherein the syringe defines a chamber containing the liquid medicament, the syringe comprises a stopper slidably arranged within the chamber and an injection needle in fluid communication with the chamber, and the needle shroud is configured to surround at least a portion of the needle when the needle shroud is in the extended position.*

*41. The auto-injector of claim 17, further comprising a syringe retainer defining a chamber configured to receive the syringe, the housing being configured to contain both the syringe retainer and the syringe disposed in the chamber of the syringe retainer.*

* * * * *